(12) United States Patent  
Sakamoto et al.

(10) Patent No.: US 8,912,487 B2  
(45) Date of Patent: Dec. 16, 2014

(54) CHARGED PARTICLE BEAM DEVICE, POSITION SPECIFICATION METHOD USED FOR CHARGED PARTICLE BEAM DEVICE, AND PROGRAM

(75) Inventors: Kunio Sakamoto, Hitachinaka (JP); Megumi Aizawa, Hitachi (JP); Satoshi Tomimatsu, Hitachinaka (JP); Isamu Sekihara, Hitachinaka (JP)

(73) Assignee: HItachi High-Technologies Corporation, Tokyo (JP)

( * ) Notice: Subject to any disclaimer, the term of this patent is extended or adjusted under 35 U.S.C. 154(b) by 109 days.

(21) Appl. No.: 13/503,074

(22) PCT Filed: Oct. 6, 2010

(86) PCT No.: PCT/JP2010/067531  
§ 371 (c)(1),  
(2), (4) Date: Apr. 20, 2012

(87) PCT Pub. No.: WO2011/048946  
PCT Pub. Date: Apr. 28, 2011

(65) Prior Publication Data  
US 2012/0211652 A1    Aug. 23, 2012

(30) Foreign Application Priority Data  
Oct. 23, 2009 (JP) ................................ 2009-244537

(51) Int. Cl.  
*H01J 37/304* (2006.01)  
*H01J 37/305* (2006.01)  
*G01N 23/22* (2006.01)  
*H01J 37/302* (2006.01)

(52) U.S. Cl.  
CPC ........ *H01J 37/3056* (2013.01); *G01N 23/2208* (2013.01); *H01J 37/302* (2013.01); *H01J 37/3045* (2013.01); *H01J 2237/31749* (2013.01); *H01J 2237/3174* (2013.01)  
USPC ........................... 250/307; 250/310; 250/309

(58) Field of Classification Search  
CPC .................................................. G01N 23/2208  
USPC .............................................. 250/306–443.1  
See application file for complete search history.

(56) References Cited

U.S. PATENT DOCUMENTS

2003/0001109 A1    1/2003    Morio et al.

FOREIGN PATENT DOCUMENTS

JP          6-260399 A      9/1994  
JP          7-230784 A      8/1995

(Continued)

OTHER PUBLICATIONS

International Search Report with English translation dated Nov. 16, 2010 (two (2) pages).

(Continued)

*Primary Examiner* — Michael Logie  
*Assistant Examiner* — Eliza Osenbaugh-Stewart  
(74) *Attorney, Agent, or Firm* — Crowell & Moring LLP

(57) ABSTRACT

Observation using an FIB image is enabled without causing any damage to a designated region. To this end, an ion beam scanning-prohibited region is set in a sample by using an image acquired by a charged particle beam other than an ion beam, or an image prepared as external data as a peripheral image including the designated region of a sample. Thereafter, the image used to set the ion beam scanning-prohibited region is exactly superimposed on an FIB image acquired for regions except the ion beam scanning-prohibited region, thereby forming an image including the ion beam scanning-prohibited region on which ion beam scanning has not been performed.

12 Claims, 15 Drawing Sheets

(56) References Cited

FOREIGN PATENT DOCUMENTS

| | | | | |
|---|---|---|---|---|
| JP | 10092364 A | * | 4/1998 | ............ H01J 37/147 |
| JP | 3240730 B2 | | 10/2001 | |
| JP | 2003-16988 A | | 1/2003 | |
| JP | 2009-139132 A | | 6/2009 | |

OTHER PUBLICATIONS

Form PCT/ISA/237 (three (3) pages).

* cited by examiner

CHARGED PARTICLE BEAM DEVICE, POSITION SPECIFICATION METHOD USED FOR CHARGED PARTICLE BEAM DEVICE, AND PROGRAM

TECHNICAL FIELD

The present invention relates to a charged particle beam device.

BACKGROUND ART

Nowadays, charged particle beam devices, such a scanning electron microscope (SEM) and an FIB (FIB: focused ion beam) device, are used for the processing, observation, and the like of semiconductor devices and other microdevices. Accordingly, there is a growing importance of processing technology that is non-damaging or less damaging to a sample or of technology that allows observation of the structure and shape of a sample surface under a non-damaging or less damaging condition. Here, the FIB device refers to a device for causing a phenomenon known as ion sputtering in which atoms in a surface are made to spring out into a vacuum by irradiating a focused ion beam to a site desired to be processed. In the FIB device, the same ion beam as used at the time of processing is used also at the time of setting a prearranged location to be processed. Thus, a location to be processed is specified on the basis of an FIB image obtained by ion beam scanning. It has been revealed, however, that the ion beam used when setting the prearranged location to be processed also causes ion sputtering as it does at the time of processing, thus causing damage to a sample.

CITATION LIST

Patent Literature

Patent Literature 1: JP Patent No. 3240730

SUMMARY OF INVENTION

Technical Problem

Hence, as the result of having made a keen examination with regard to a method for precisely specifying a prearranged location to be processed, without using any observed images obtained by ion beam scanning, the inventors of the present application have gained the knowledge described below.

Conventionally, a region assumed to include a prearranged location to be processed is scanned with an ion beam, and the prearranged location is specified from an FIB image obtained by this scanning and set as a location to be processed, in order to precisely specify the prearranged location to be processed. As described above, however, damage is caused to sample surfaces due to ion beam scanning at the time of obtaining the FIB image. If this damage occurs, there arises the problem of being no longer possible to precisely observe the sample surfaces.

In contrast, use of an SEM image obtained by electron beam scanning or an image captured from the outside to specify a prearranged location to be processed can reduce the possibility of causing damage to a sample. These images differ, however, from images obtained based on an ion beam used in actual processing. Accordingly, these images are not the same as images obtained based on the actually-used ion beam. In addition, if the scan angles of the FIB image and the captured image including the SEM image with respect to the sample differ from each other, distortions occur unavoidably even if the same sample is observed.

The present invention is intended to enable the understanding of the condition of a sample and the precise processing or observation of a designated location, without causing any damage to the prearranged location of the sample to be processed.

Solution to Problem

The present invention is configured to complementarily superimpose and display a first image obtained by scanning a scanning region set by excluding an ion beam irradiation-prohibited region with an ion beam, and a second image corresponding to a capturing region including the ion beam irradiation-prohibited region and set so as to overlap with part of the scanning region. Here, the second image is an image acquired by means of scanning using a charged particle beam other than an ion beam or by means of capture from the outside.

Advantageous Effects of Invention

According to the present invention, it is possible to observe the conditions of an irradiation-prohibited region being processed or observed and the periphery thereof by using the same image as an FIB image, without causing any damage to the irradiation-prohibited region by an ion beam.

DESCRIPTION OF EMBODIMENTS

Hereinafter, embodiments of the present invention will be described according to the accompanying drawings. Note that details on the device configurations and processing operations to be described hereinafter are given for the purpose of describing the present invention, and therefore, are illustrative only. Accordingly, the present invention also encompasses any inventions made by combining known technologies with the later-described device configurations and processing operations or by substituting some of the later-described device configurations and processing operations by the known technologies.

(1) Embodiment 1

(1-1) Device Configuration

Figure 1:
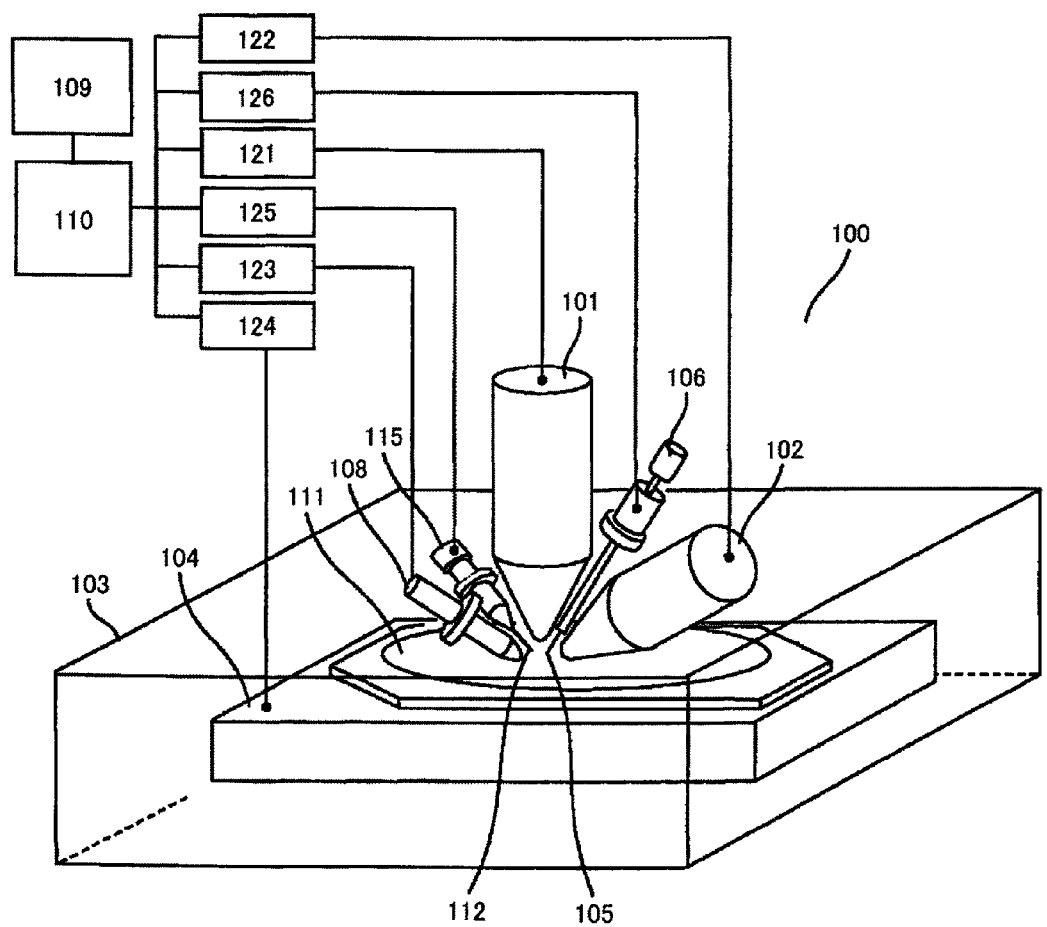
FIG. 1 is a drawing illustrating a configuration example of a composite charged particle beam device.

FIG. 1 is a simplified drawing of a charged particle beam device according to the embodiment. Note that in FIG. 1, part of the device is drawn transparently. A charged particle beam device 100 is one example of a so-called composite device.

The charged particle beam device 100 is provided with a focused ion beam column 101 for generating a ion beam used to observe and process a sample and a probe, an electron beam column 102 for generating an electron beam used to observe surface shapes of the sample and the probe, a vacuum sample chamber 103, a sample stage 104 to be mounted with the sample, a probe driver 106 for finely moving a probe 105 within the vacuum sample chamber 103, a detector 108, a deposition gas source 115, a display 109, and a computing processor 110.

The focused ion beam column 101 focuses ions generated in an ion source (not illustrated) into a beam and irradiates the beam to a sample 111 and the probe 105, thereby enabling surfaces of the sample 111 and the probe 105 to be observed or processed. In addition, the electron beam column 102 turns electrons generated in an electron source (not illustrated) into a beam and irradiates the beam to the sample 111 and the probe 105, thereby enabling surfaces of the sample 111 and the probe 105 to be observed.

By disposing both columns, so that the irradiation position of an electron beam emitted from the electron beam column 102 is almost the same as the position of ion-beam irradiation from the focused ion beam column 101, a portion to be processed by an ion beam can be observed using the electron beam. In FIG. 1, the focused ion beam column 101 is disposed in a direction perpendicular to the sample 111, and the electron beam column 102 is disposed in a direction inclined with respect to the sample 111. However, an example of arrangement of the two columns is not limited to the one illustrated in FIG. 1. For example, the electron beam column 102 may be disposed in a direction perpendicular to the sample 111, and the focused ion beam column 101 may be disposed so as to be inclined with respect to the sample 111.

The sample stage 104 can be mounted with the sample 111, and can move a location necessary to be processed or observed with an ion beam to an ion-beam irradiation position, or move the location to an electron beam-based observation position. Note that the sample 111 is assumed to be iron, steel, light metal, a polymeric high molecule, and the like, in addition to a semiconductor sample.

The probe 105 is enabled by the probe driver 106 to move within the vacuum sample chamber 103, and is used to, for example, extract a minuscule test piece formed in the sample or supply a potential to the sample by bringing the probe into contact with a sample surface. The deposition gas source 115 stores a deposition gas for forming a deposited film by the irradiation of a charged particle beam. The deposition gas source 115 can supply the deposition gas, as necessary, from a nozzle tip 112.

The detector 108 is used to detect secondary electrons, secondary ions, backscattered electrons, X-rays, reflection electrons, and the like (also referred to simply as "particles" in this specification) generated from the irradiated part of a sample, a probe or the like by the irradiation of an ion beam or an electron beam. Detected signals of these particles are turned into images through arithmetic processing by the computing processor 110. The images are shown on the display 109 as secondary electron images, secondary ion images, elemental maps based on characteristic X-rays, or the like. Alternatively, transmitted electrons may be converted into secondary electrons and detected by the detector 108, or transmitted electrons may also be detected using an unillustrated detector.

The computing processor 110 controls the focused ion beam column 101, the electron beam column 102, the detector 108, the sample stage 104, the deposition gas source 115, and the probe driver 106 through ion beam control means 121, electron beam control means 122, detector control means 123, stage control means 124, deposition gas source control means 125, and probe control means 126, respectively.

(1-2) Data Flow Associated with Image Superimposition Processing

Figure 2:
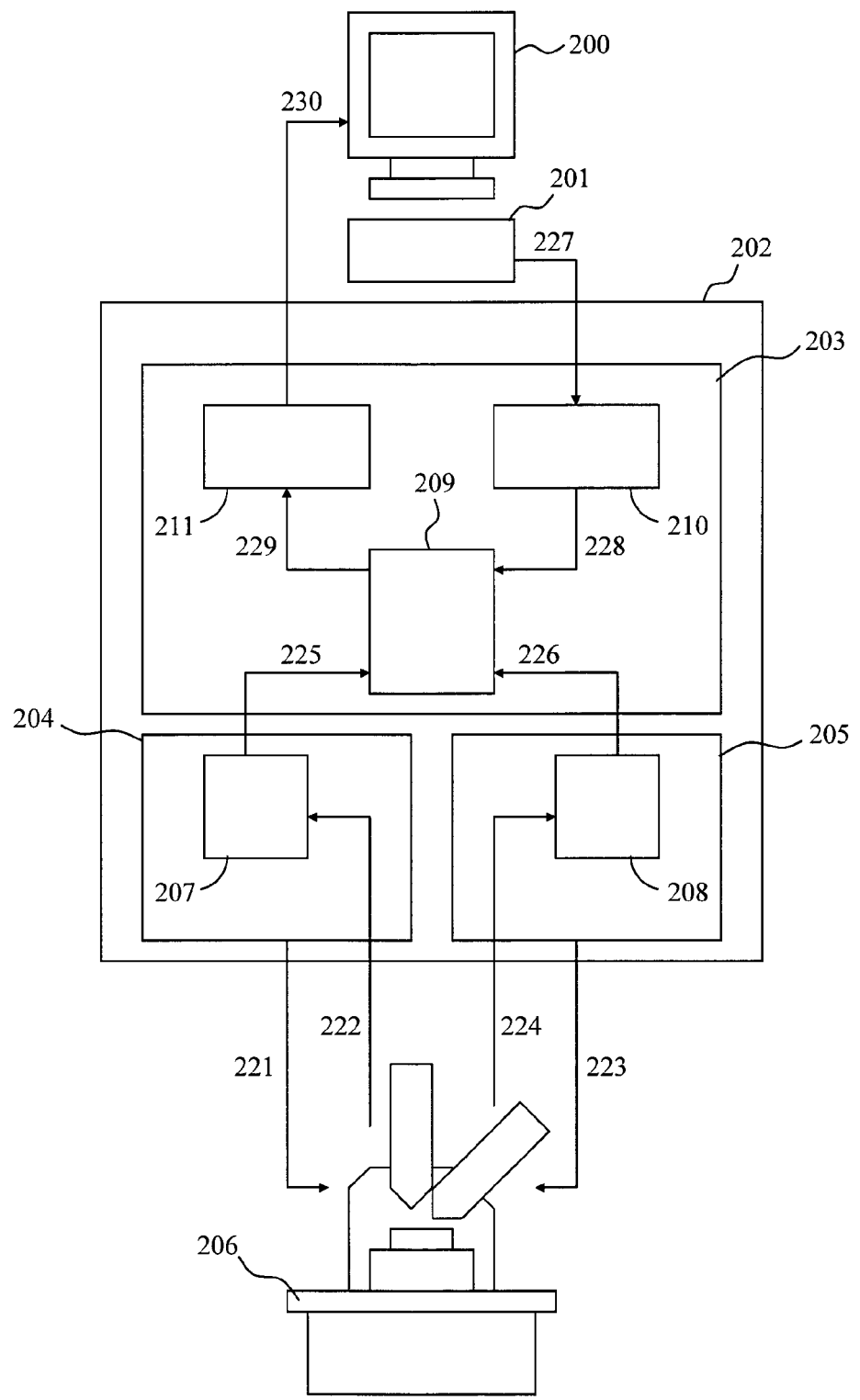
FIG. 2 is a drawing used to describe an overview of image superimposition processing.

FIG. 2 is a conceptual drawing of image superimposition processing used in the embodiment. FIG. 2 represents a device configuration and a process flow in association with each other.

The charged particle beam device is provided with a display unit 200, an input unit 201, a control unit 202, and a device main unit 206. The control unit 202 is provided with a GUI controller 203, an FIB controller 204, and an SEM controller 205.

First, a control signal 221 is sent from the FIB controller 204 to the device main unit 206. Consequently, the luminance data 222 of an FIB is stored in an FIB image memory 207. Likewise, a control signal 223 is sent from the SEM controller 205 to the device main unit 206. Consequently, the luminance data 224 of an SEM is stored in an SEM image memory 208.

The GUI controller 203 acquires FIB image data 225 from the FIB image memory 207 and SEM image data 226 from the SEM image memory 208. In addition, the input unit 201 transmits an input signal 227 reflecting a user's operating input to input control 210. The input control 210 acquires information 228 on a superimposing position, an angle, scale data, and the like on the basis of the input signal 227. By image superimposition control 209 based on these pieces of the information 228, an FIB image and an SEM image are superimposed to create superimposed image data 229. Image display control 211 converts the superimposed image data 229 into a display signal 230, sends the display signal 230 to the display unit 200, and displays an image on the screen of the display unit 200.

(1-3) Concept of Image Superimposition Processing

In this embodiment, a description will be given of a method for specifying a location to be processed without scanning an ion beam through peripheral positions in a prearranged region to be processed, in a case where the deflection direction of the ion beam and the tilt axis of the sample 111 are perpendicular to each other.

Figure 3:
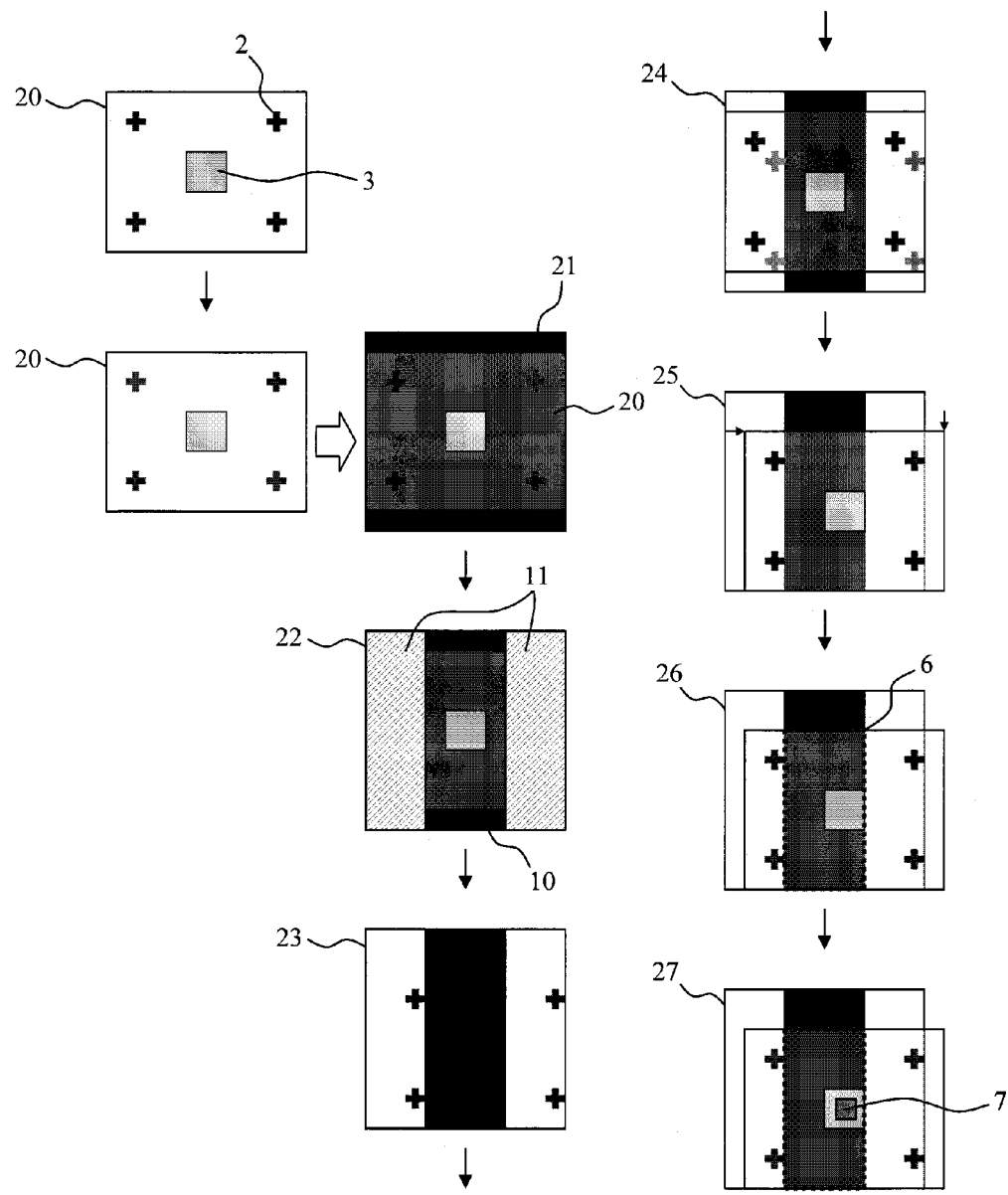
FIG. 3 is a drawing used to describe a procedure for specifying a location to be processed, while excluding the periphery of a prearranged region to be processed from an ion beam-scanned region.

Hereinafter, the concept of image superimposition processing will be described using FIG. 3. In FIG. 3, an image, such as an SEM image, captured using a nondestructive beam is shown as a captured image 20. The captured image 20 includes four images of singular points 2. As the singular points 2, patterns formed on a sample, for example, are used. If there are no singular points 2, a sample surface may be previously processed using an FIB to create marks, and these marks may be alternatively used as the singular points 2. Note that examples of images captured from the outside include a charged particle beam image taken as design data or taken in other processes. A device operator determines an approximate position of a prearranged region to be processed within the captured image 20, and designates an ion beam irradiation-prohibited region 3 in the prearranged region to be processed thus determined. After this, the charged particle beam device 100 displays an image 21 provided by superimposing the image 20 in which the ion beam irradiation-prohibited region 3 is designated on an FIB image 4 (which has not yet been taken in this phase and is, therefore, shown as an area marked out in black).

The device operator designates a non-ion beam scanned region 10, including the ion beam irradiation-prohibited region 3, while visually observing the image 21. At the same time, the device operator sets the rest of the regions of the FIB image 4, excluding the non-ion beam scanned region 10, as ion beam-scanned regions 11 (image 22).

After this, the charged particle beam device 100 scans the ion beam-scanned regions 11 designated in the image 22 with an ion beam to acquire an FIB image 23. Next, the charged particle beam device 100 displays an image 24, in which the acquired FIB image 23 and the captured image 20 are superimposed, on the display 109.

The device operator moves the captured image 20 from side to side and up and down, while paying attention to the acquired FIB image 23 and the singular points 2 included in the captured image 20, so as to eliminate the misalignment of the images with each other, thereby superimposing the images on each other (image 25). In the case of FIG. 3, four singular points 2 each are included in the captured image 20 and the FIB image 23, respectively. Desirably, three or more singular points 2 are included in each image, though this depends on the shape and layout of the singular points 2. The charged particle beam device 100 may automatically perform the alignment of singular points with one another discussed here through image processing.

By this alignment, the charged particle beam device 100 generates an image 26 in which some of missing regions (including the prearranged region to be processed) of the FIB image are complemented with a captured image 20 (complementary image 6) acquired as an SEM image or external data.

The device operator specifies a region 7 to be processed, while visually observing the image 26 shown on the display 109.

(1-4) Conclusion

According to Embodiment 1, the irradiation of an ion beam to the region 7 to be processed can be limited to a case of actually processing a sample. Consequently, damage to the region 7 to be processed at the time of observation can be avoided using the charged particle beam device 100 according to Embodiment 1. On the other hand, in the case of the background art, an ion beam is irradiated to the region 7 to be processed both at the time of setup and at the time of processing. Accordingly, it has been unavoidable to cause damage to the region 7 to be processed prior to processing.

In addition, Embodiment 1 employs a technique for aligning an SEM image or a captured image 1 acquired from the outside with the FIB image 23. Accordingly, the position coordinates of the region 7 to be processed can be determined as precise position coordinates for the focused ion beam column 101 used in actual processing. As a result, a desired pattern can be precisely processed in a precise position.

(2) Embodiment 2

Subsequently, a description will be given of an example of processing operation employed in a charged particle beam device according to Embodiment 2. Embodiment 2 is a modified example of Embodiment 1. In Embodiment 2, a description will be given of another example of processing operation at the time of superimposing a captured image 1, such as an SEM image, on an FIB image 23.

Figure 4:
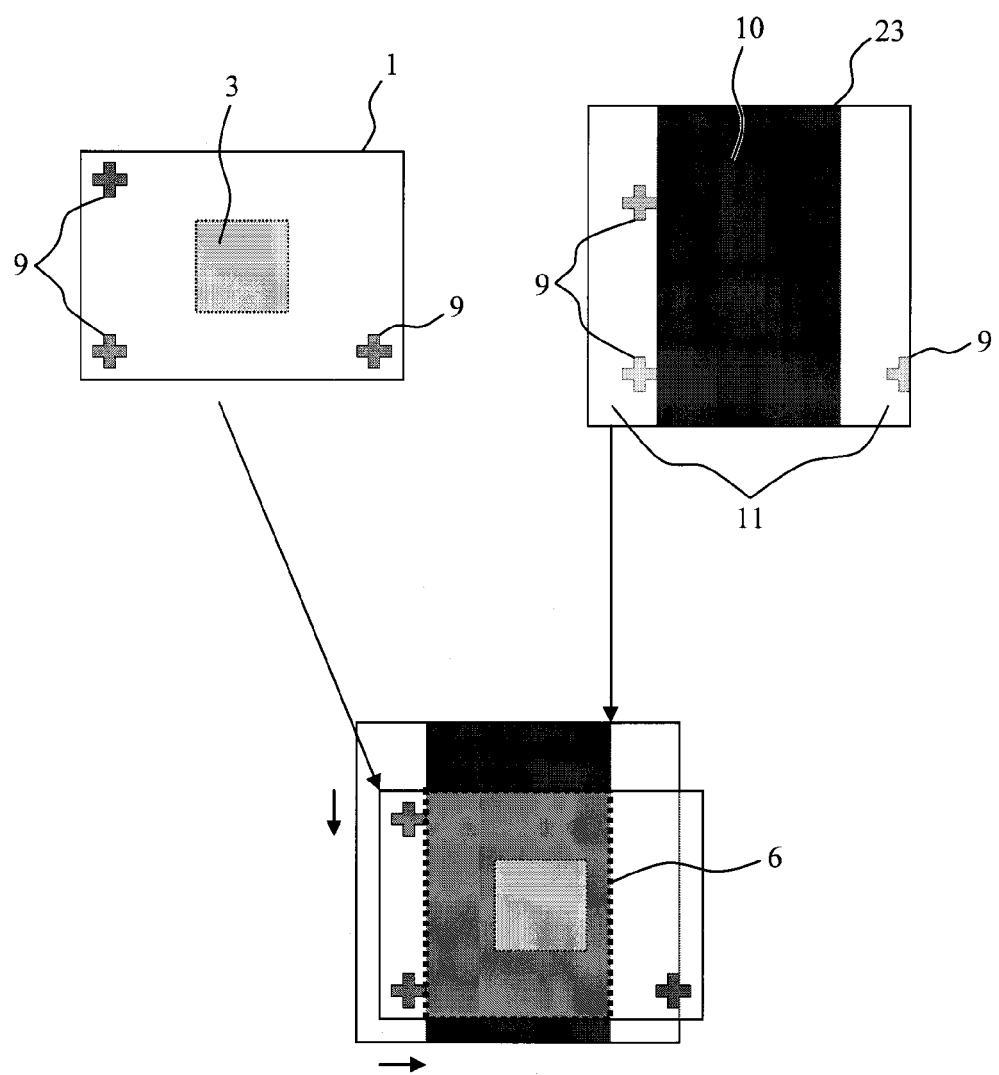
FIG. 4 is a drawing used to describe the superimposition of a captured image with an FIB image by moving the captured image.

FIG. 4 illustrates the way the captured image 1 is moved onto the FIB image 23 to superimpose the two images. This Embodiment 2 is the same in basic processing operation as Embodiment 1.

That is, the captured image 1 including an ion beam irradiation-prohibited region 3 and singular points 9 and the FIB image 23 in which a non-ion beam scanned region 10 and ion beam-scanned regions 11 are designated are superimposed on each other. Specifically, the captured image 1 is moved up and down and/or from side to side, so that the singular points 9 included in the captured image 1 overlap with singular points 9 included in the FIB image 23. Consequently, there is obtained an image in which the non-ion beam scanned region 10 is complemented with the captured image 1, so that the singular points 9 of the captured image 1 and the singular points 9 of the FIB image 23 align with one another.

Figure 5:
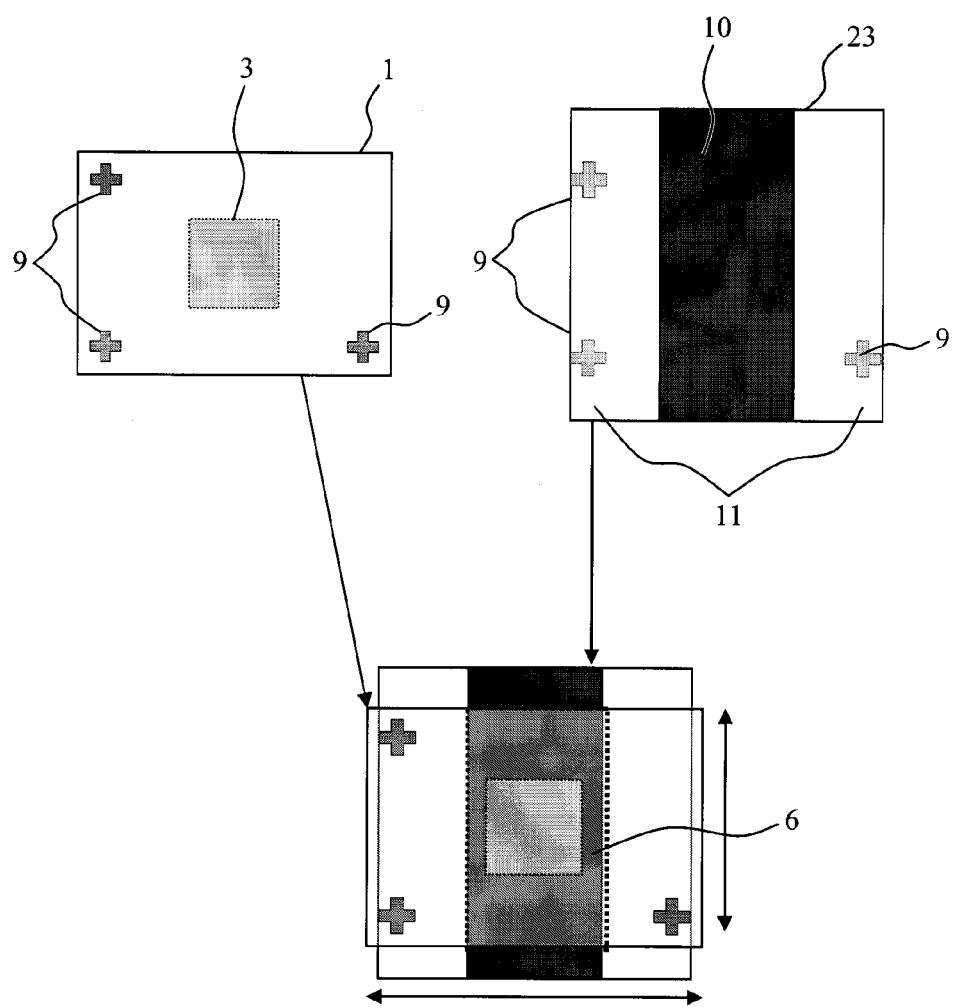
FIG. 5 is a drawing used to describe the superimposition of a captured image with an FIB image by enlarging the captured image.

Incidentally, in the case of FIG. 4, the size of each singular point 9 of the captured image 1 and the size of each singular point 9 of the FIB image 23 do not always agree with each other. In such a case, the charged particle beam device 100 according to Embodiment 2 enlarges the captured image 1 in a vertical direction and/or in a horizontal direction by means of image processing, as illustrated in FIG. 5. Thus, the singular points 9 of the captured image 1 after scale change and the singular points 9 of the FIB image 23 are made to agree in size with each other. Desirably, the charged particle beam device 100 automatically performs this processing. After scale change, the charged particle beam device 100 completes an image in which part of the non-ion beam scanned region 10 of the FIB image 23 is complemented with the captured image 1.

Figure 6:
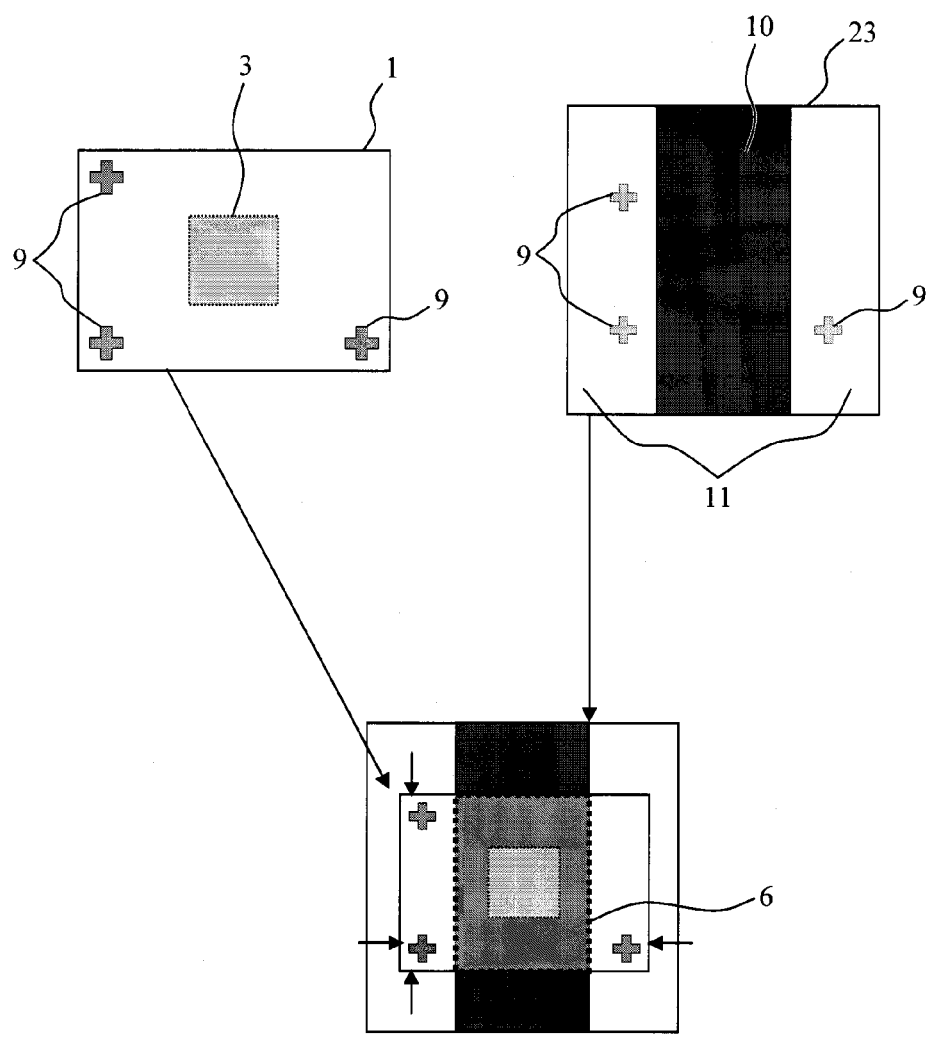
FIG. 6 is a drawing used to describe the superimposition of a captured image with an FIB image by shrinking the captured image.

Note that the change of an image size is not limited only to enlarging the captured image 1. FIG. 6 illustrates an example of making the scale of the captured image 1 and the scale of the FIB image 23 agree with each other by shrinking the captured image 1. In the case of FIG. 6, the charged particle beam device 100 shrinks the captured image 1 in a vertical direction and/or in a horizontal direction to make the singular points 9 of the captured image 1 after scale change and the singular points 9 of the FIB image 23 agree in size with each other. Thus, the charged particle beam device 100 completes an image in which part of the non-ion beam scanned region 10 is complemented with the captured image 1.

Figure 7:
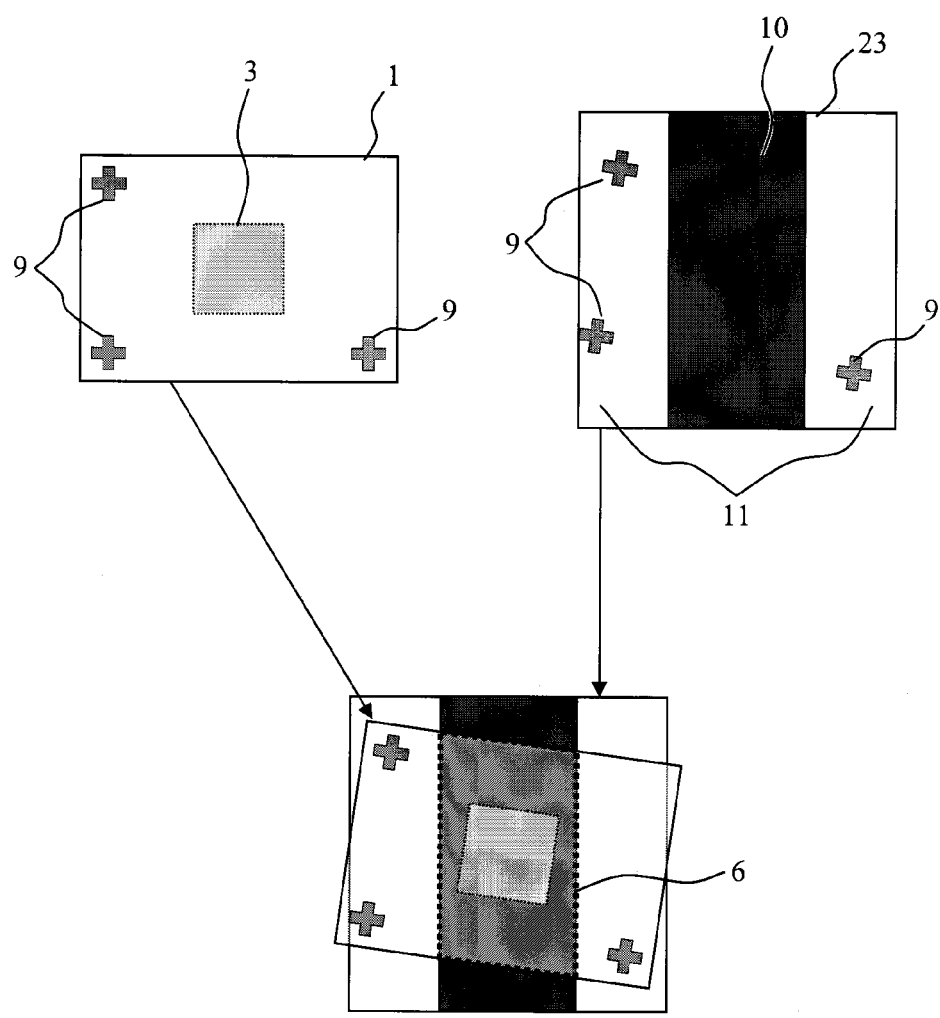
FIG. 7 is a drawing used to describe the superimposition of a captured image with an FIB image by rotating the captured image.

In addition, it is also assumed that even if the captured image 1 and the FIB image 23 agree in scale with each other, the inclinations of the respective images do not agree with each other. In such a case, the charged particle beam device 100 rotates the captured image 1 clockwise or counterclockwise, as illustrated in FIG. 7, so as to align the singular points 9 of the captured image 1 and the singular points 9 of the FIB image 23 with one another. Thus, the charged particle beam device 100 completes the image in which part of the non-ion beam scanned region 10 is complemented with the captured image 1.

By utilizing these superimposition techniques either independently or in combination, the two images can be precisely aligned with each other even if the captured image 1 corresponding to a periphery of the region 7 to be processed and the FIB image 23 do not agree in initial scale or inclination with each other.

(3) Embodiment 3

Subsequently, a description will be given of examples of processing operation employed in a charged particle beam device according to Embodiment 3. Embodiment 3 is also a modified example of Embodiment 1. In this embodiment, a description will be given of other examples of setting a non-ion beam scanned region 10 or ion beam-scanned regions 11. As described above, the ion beam-scanned regions 11 need to be set in positions clear of an ion beam irradiation-prohibited region 3.

Figure 8:
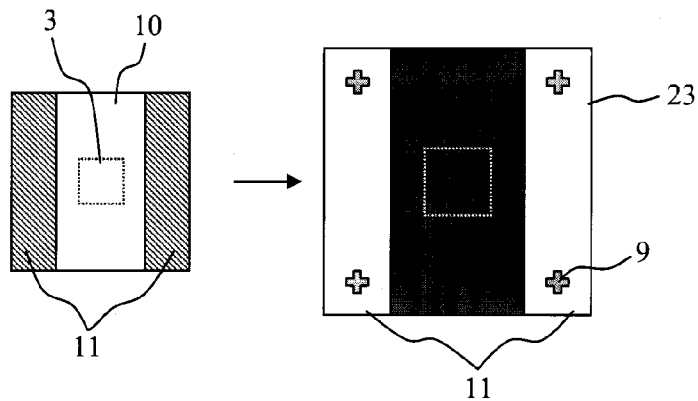
FIG. 8 is a drawing used to describe an example of setting ion beam-scanned regions on the right and left sides of an ion beam irradiation-prohibited region.

In the above-described embodiment, a description has been given of an example of setting belt-like ion beam-scanned regions 11 (FIB image acquisition regions) extending in a vertical direction in the figure on both sides of the ion beam irradiation-prohibited region 3, as illustrated in FIG. 8. Note that the widths of the ion beam-scanned regions 11 and the non-ion beam scanned region 10 in the horizontal direction thereof (horizontal lengths) may be either fixed or arbitrarily variable in response to the operating input of a device operator.

Figure 9:
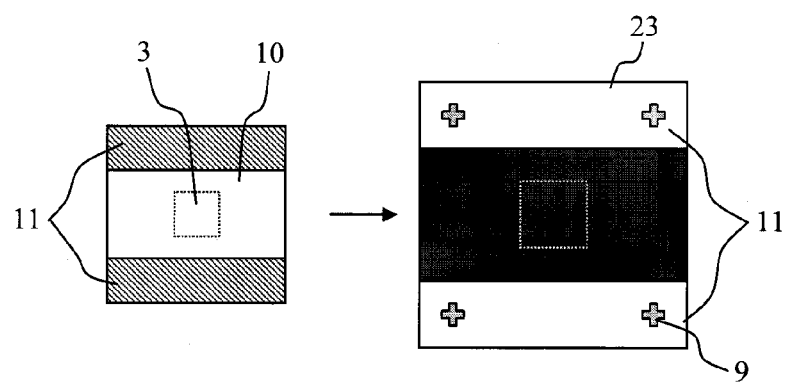
FIG. 9 is a drawing used to describe an example of setting ion beam-scanned regions on the upper and lower sides of an ion beam irradiation-prohibited region.

Alternatively, as illustrated in FIG. 9, it is also possible to set belt-like ion beam-scanned regions 11 extending in a horizontal direction in the figure on both the upper and lower sides of the ion beam irradiation-prohibited region 3. Also in this case, the heights of the ion beam-scanned regions 11 and the non-ion beam scanned region 10 in the vertical direction thereof (vertical lengths) may be either fixed or arbitrarily variable in response to the operating input of the device operator.

Figure 10:
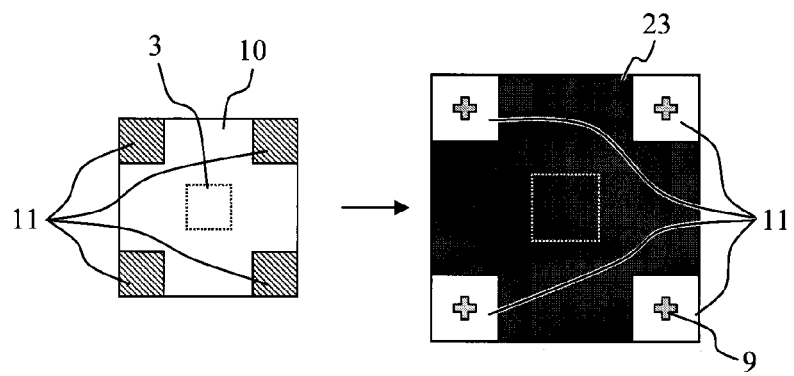
FIG. 10 is a drawing used to describe an example of setting ion beam-scanned regions in four corners within an ion beam irradiation-permitted area excluding an ion beam irradiation-prohibited region.

Yet alternatively, as illustrated in FIG. 10, it is also possible to set only the four corners of an ion beam irradiation-permitted area, except the ion beam irradiation-prohibited region 3, as ion beam-scanned regions 11, and set the rest of regions as the non-ion beam scanned region 10. In the case of FIG. 10, the number of ion beam-scanned regions 11 is 4. Also in this case, the heights (vertical lengths) and widths (horizontal lengths) of the ion beam-scanned regions 11 and the non-ion beam scanned region 10 may be either fixed or arbitrarily variable in response to the operating input of the device operator.

Figure 11:
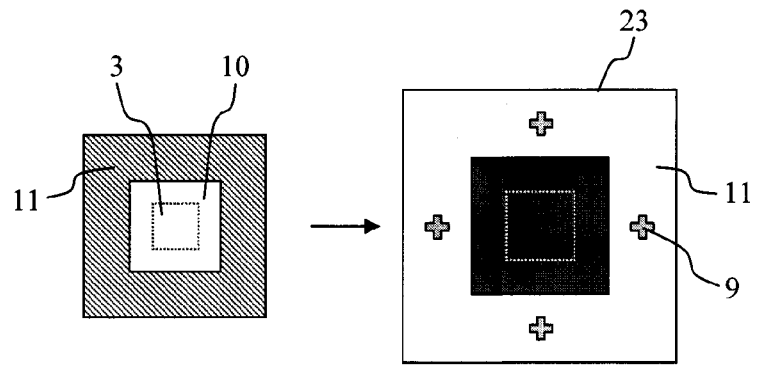
FIG. 11 is a drawing used to describe an example of setting an ion beam-scanned region, so as to surround an ion beam irradiation-prohibited region.

Still alternatively, as illustrated in FIG. 11, it is also possible to circumferentially set an ion beam-scanned region 11, so as to surround the entire ion beam irradiation-prohibited region 3, and set the non-ion beam scanned region 10 inside the ion beam-scanned region 11. Also in this case, the heights (vertical lengths) and widths (horizontal lengths) of the ion beam-scanned regions 11 and the non-ion beam scanned region 10 may be either fixed or arbitrarily variable in response to the operating input of the device operator.

Figure 12:
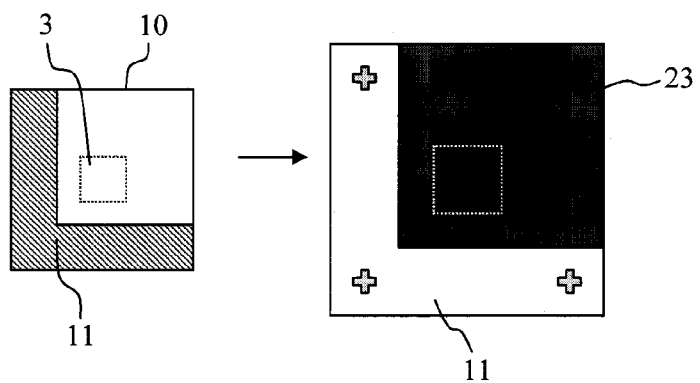
FIG. 12 is a drawing used to describe an example of setting ion beam-scanned regions in an L-shaped manner (on the left and lower sides) outside an ion beam irradiation-prohibited region.

Still alternatively, as illustrated in FIG. 12, it is also possible to set belt-like (L-shaped) ion beam-scanned regions 11 on the left and lower sides of the ion beam irradiation-prohibited region 3, respectively, and set the rest of regions as the non-ion beam scanned region 10. In the case of FIG. 12, the widths and heights of regions giving an L-shape may be either fixed or arbitrarily variable in response to the operating input of the device operator.

Figure 13:
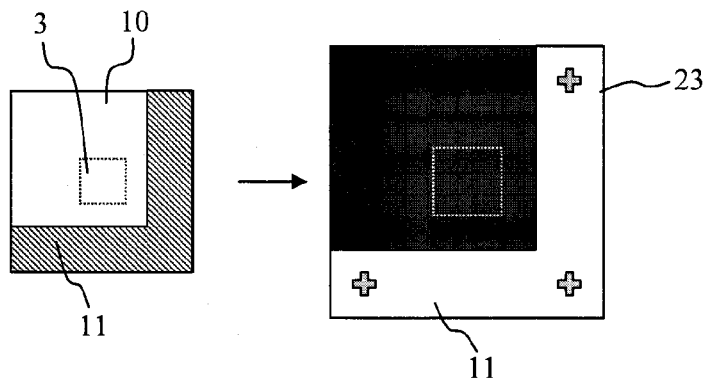
FIG. 13 is a drawing used to describe an example of setting ion beam-scanned regions in an L-shaped manner (on the right and lower sides) outside an ion beam irradiation-prohibited region.

Still alternatively, as illustrated in FIG. 13, it is also possible to set belt-like (L-shaped) ion beam-scanned regions 11 on the right and lower sides of the ion beam irradiation-prohibited region 3, respectively, and set the rest of regions as the non-ion beam scanned region 10. In the case of FIG. 13, the widths and heights of regions giving an L-shape may be either fixed or arbitrarily variable in response to the operating input of the device operator.

Figure 14:
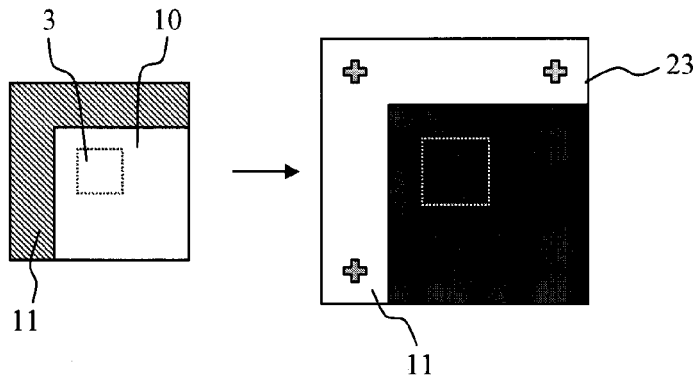
FIG. 14 is a drawing used to describe an example of setting ion beam-scanned regions in an L-shaped manner (on the left and upper sides) outside an ion beam irradiation-prohibited region.

Still alternatively, as illustrated in FIG. 14, it is also possible to set belt-like (L-shaped) ion beam-scanned regions 11 on the left and upper sides of the ion beam irradiation-prohibited region 3, respectively, and set the rest of regions as the non-ion beam scanned region 10. In the case of FIG. 14, the widths and heights of regions giving an L-shape may be either fixed or arbitrarily variable in response to the operating input of the device operator.

Figure 15:
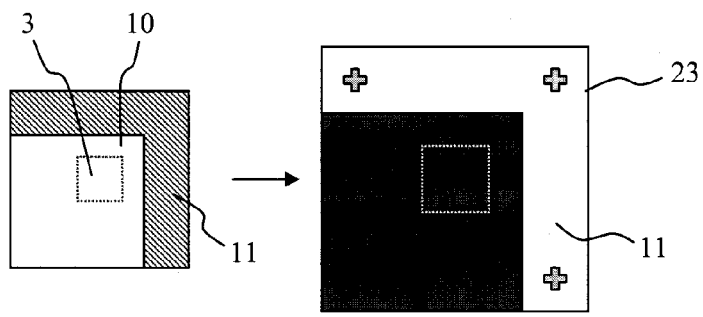
FIG. 15 is a drawing used to describe an example of setting ion beam-scanned regions in an L-shaped manner (on the right and upper sides) outside an ion beam irradiation-prohibited region.

Still alternatively, as illustrated in FIG. 15, it is also possible to set belt-like (L-shaped) ion beam-scanned regions 11 on the right and upper sides of the ion beam irradiation-prohibited region 3, respectively, and set the rest of regions as the non-ion beam scanned region 10. In the case of FIG. 15, the widths and heights of regions giving an L-shape may be either fixed or arbitrarily variable in response to the operating input of the device operator.

Figure 16:
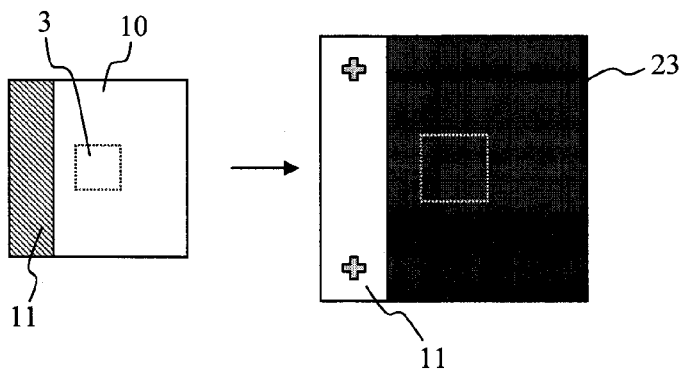
FIG. 16 is a drawing used to describe an example of setting an ion beam-scanned region on the left side outside an ion beam irradiation-prohibited region.

Still alternatively, as illustrated in FIG. 16, it is also possible to set a belt-like ion beam-scanned region 11 only on the left side of the ion beam irradiation-prohibited region 3, and set the rest of regions as the non-ion beam scanned region 10. In the case of FIG. 16, the width and height of the ion beam-scanned region 11 may be either fixed or arbitrarily variable in response to the operating input of the device operator. Note that the number of singular points 2 is 2 in the case of FIG. 16.

Figure 17:
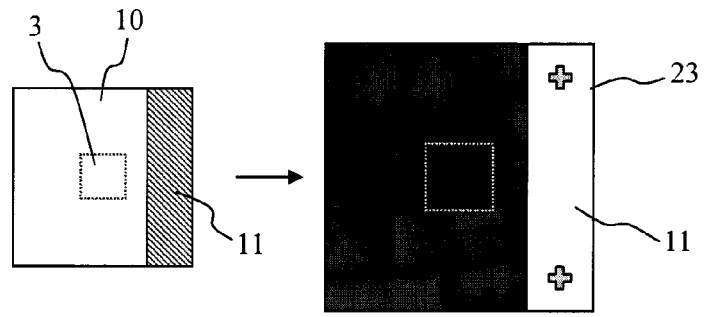
FIG. 17 is a drawing used to describe an example of setting an ion beam-scanned region on the right side outside an ion beam irradiation-prohibited region.

Still alternatively, as illustrated in FIG. 17, it is also possible to set a belt-like ion beam-scanned region 11 only on the right side of the ion beam irradiation-prohibited region 3, and set the rest of regions as the non-ion beam scanned region 10. In the case of FIG. 17, the width and height of the ion beam-scanned region 11 may be either fixed or arbitrarily variable in response to the operating input of a device operator. Note that the number of singular points 2 is 2 also in the case of FIG. 17.

Figure 18:
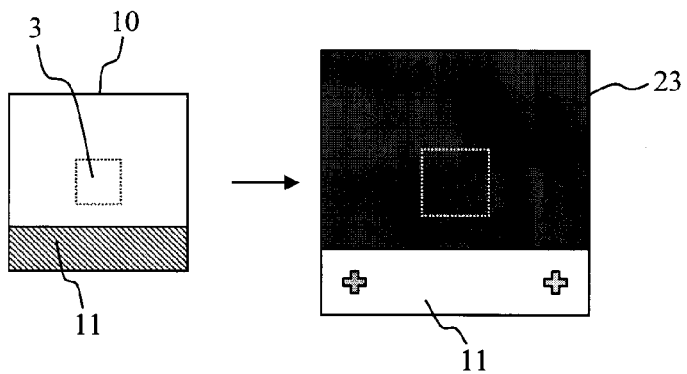
FIG. 18 is a drawing used to describe an example of setting an ion beam-scanned region on the lower side outside an ion beam irradiation-prohibited region.

Still alternatively, as illustrated in FIG. 18, it is also possible to set a belt-like ion beam-scanned region 11 only on the lower side of the ion beam irradiation-prohibited region 3, and set the rest of regions as the non-ion beam scanned region 10. In the case of FIG. 18, the width and height of the ion beam-scanned region 11 may be either fixed or arbitrarily variable in response to the operating input of the device operator. Note that the number of singular points 2 is 2 also in the case of FIG. 18.

Figure 19:
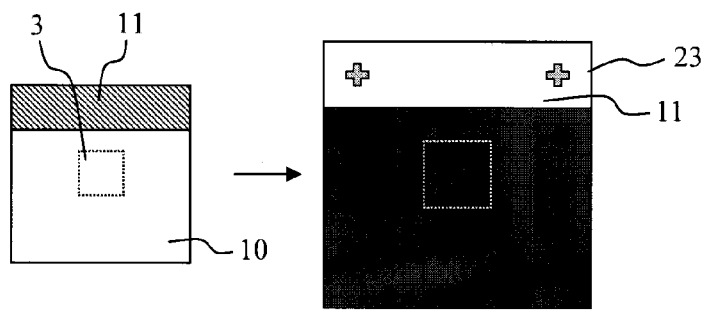
FIG. 19 is a drawing used to describe an example of setting an ion beam-scanned region on the upper side outside an ion beam irradiation-prohibited region.

Still alternatively, as illustrated in FIG. 19, it is also possible to set a belt-like ion beam-scanned region 11 only on the upper side of the ion beam irradiation-prohibited region 3, and set the rest of regions as the non-ion beam scanned region 10. In the case of FIG. 19, the width and height of the ion beam-scanned region 11 may be either fixed or arbitrarily variable in response to the operating input of the device operator. Note that the number of singular points 2 is 2 also in the case of FIG. 19.

Figure 20:
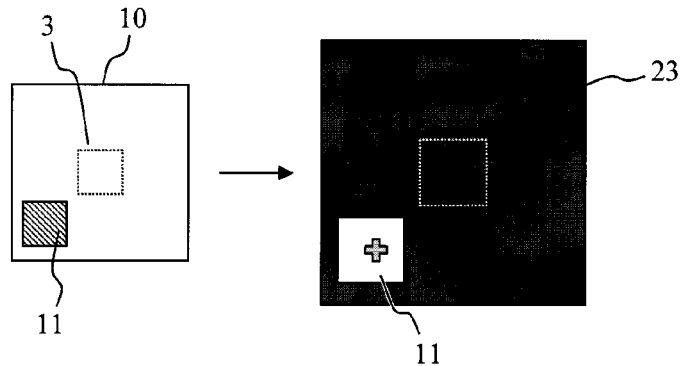
FIG. 20 is a drawing used to describe an example of setting an ion beam-scanned region in one place outside an ion beam irradiation-prohibited region.

Still alternatively, as illustrated in FIG. 20, it is also possible to set a rectangular ion beam-scanned region 11 only in the lower-left corner of the outer circumferential area of the ion beam irradiation-prohibited region 3, and set the rest of regions as the non-ion beam scanned region 10. In the case of FIG. 20, the width and height of the ion beam-scanned region 11 may be either fixed or arbitrarily variable in response to the operating input of the device operator. Note that the rectangular ion beam-scanned region 11 can also be set in the upper-left corner, the upper-right corner, or the lower-right corner. The number of singular points 2 is 1 in the case of FIG. 20.

Figure 21:
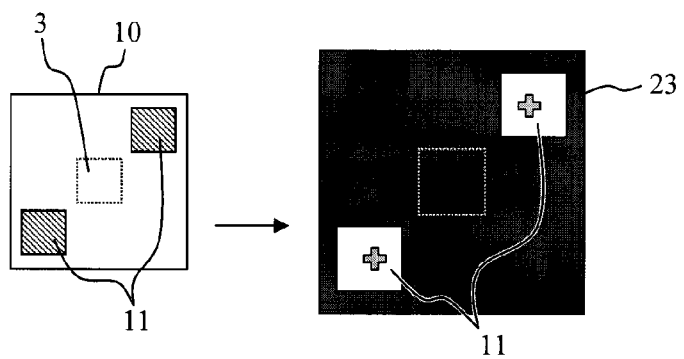
FIG. 21 is a drawing used to describe an example of setting ion beam-scanned regions in two corners (lower-left and upper-right corners) outside an ion beam irradiation-prohibited region.

Still alternatively, as illustrated in FIG. 21, it is also possible to set rectangular ion beam-scanned regions 11 in the lower-left and upper-right corners of the outer circumferential area of the ion beam irradiation-prohibited region 3, and set the rest of regions as the non-ion beam scanned region 10. In the case of FIG. 21, the width and height of each ion beam-scanned region 11 may be either fixed or arbitrarily variable in response to the operating input of the device operator. Note that three or more rectangular ion beam-scanned regions 11 can also be laid out in the outer circumferential area.

Figure 22:
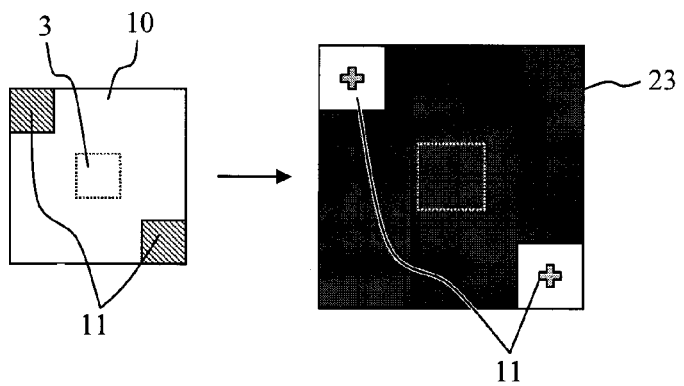
FIG. 22 is a drawing used to describe an example of setting an ion beam-scanned region in two corners (upper-left and lower-right corners) outside an ion beam irradiation-prohibited region.

Still alternatively, as illustrated in FIG. 22, it is also possible to set rectangular ion beam-scanned regions 11 in the upper-left and lower-right corners of the outer circumferential area of the ion beam irradiation-prohibited region 3, and set the rest of regions as the non-ion beam scanned region 10. In the case of FIG. 22, the width and height of each ion beam-scanned region 11 may be either fixed or arbitrarily variable in response to the operating input of the device operator.

(4) Embodiment 4

In the above-described embodiment, a description has been given on the assumption that a difference between the direction of observation based on an ion beam and the direction of observation based on an electron beam is substantially negligible. Cases are conceivable, however, in which the difference in the direction of observation is not negligible or superimposition with higher accuracy is required. A charged particle beam device according to Embodiment 4 assumes such cases as described above.

Figure 23:
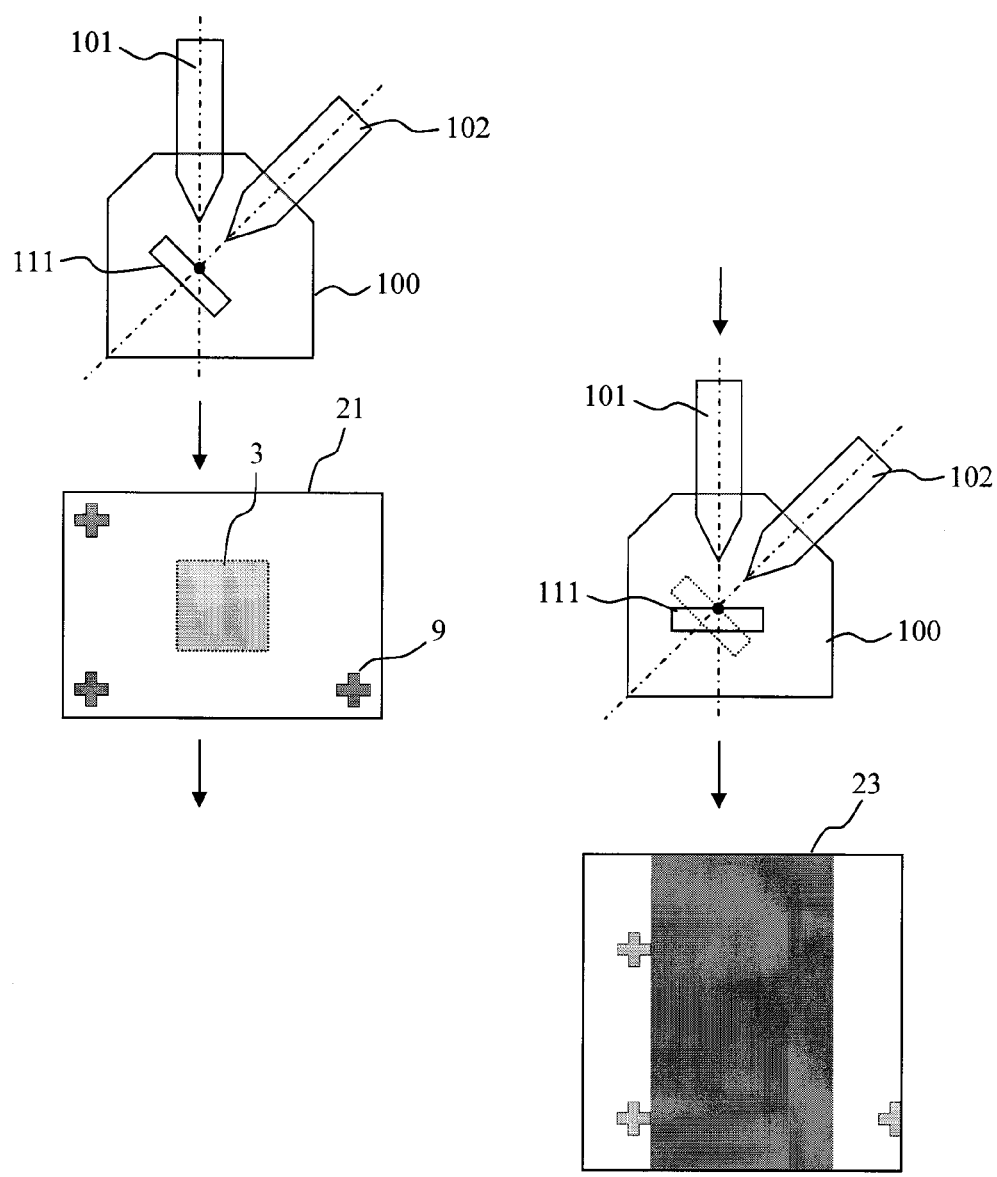
FIG. 23 is a drawing used to describe an example of capturing an SEM image and an FIB image by means of the tilt angle adjustment of a sample stage.

FIG. 23 illustrates a method for acquiring an SEM image and an FIB image facing to a sample 111 by performing an angular correction to the beam axis of a sample stage 104 (sample 111) in a charged particle beam device 100 including an electron beam column 102 and a focused ion beam column 101.

First, the sample stage 104 is inclined using an unillustrated drive mechanism at the time of acquiring the SEM image, so that the beam axis of the electron beam column 102 and the sample 111 (shown by a solid line in the figure) are perpendicular to each other. Note that the tilt angle of the sample stage 104 is realized through the control of the drive mechanism by stage control means 124. Also note that control of the tilt angle is realized through the rotational control of the sample stage 104 around three axes in horizontal directions (X-axis and Y-axis) and in a vertical direction (Z-axis) and the movement control of the sample stage 104 in the three-axis directions.

By scanning the sample 111 with an electron beam in a state where the sample 111 and the beam axis of the electron beam column 102 are aligned perpendicularly to each other and acquiring an SEM image 21 including singular points 9 and an ion beam irradiation-prohibited region 3, it is possible to acquire an image free from effects of distortion due to inclination.

Next, the sample stage 104 is inclined by an unillustrated drive mechanism at the time of acquiring the FIB image, so that the beam axis of the focused ion beam column 101 and the sample 111 (shown by a dashed line in the figure) are perpendicular to each other. In the case of FIG. 23, the sample stage 104 is rotated counterclockwise in the figure from a position set at the time of acquiring the SEM image. Also in this case, it is possible to acquire an FIB image 23 free from effects of distortion due to inclination.

In the case of FIG. 23, neither the SEM image 21 nor the FIB image 23 contains distortions. Consequently, an image precisely representing the surface condition of the sample 111 can be shown on a display 109, even if the two images are superimposed without making any tilt corrections by image processing.

Figure 24:
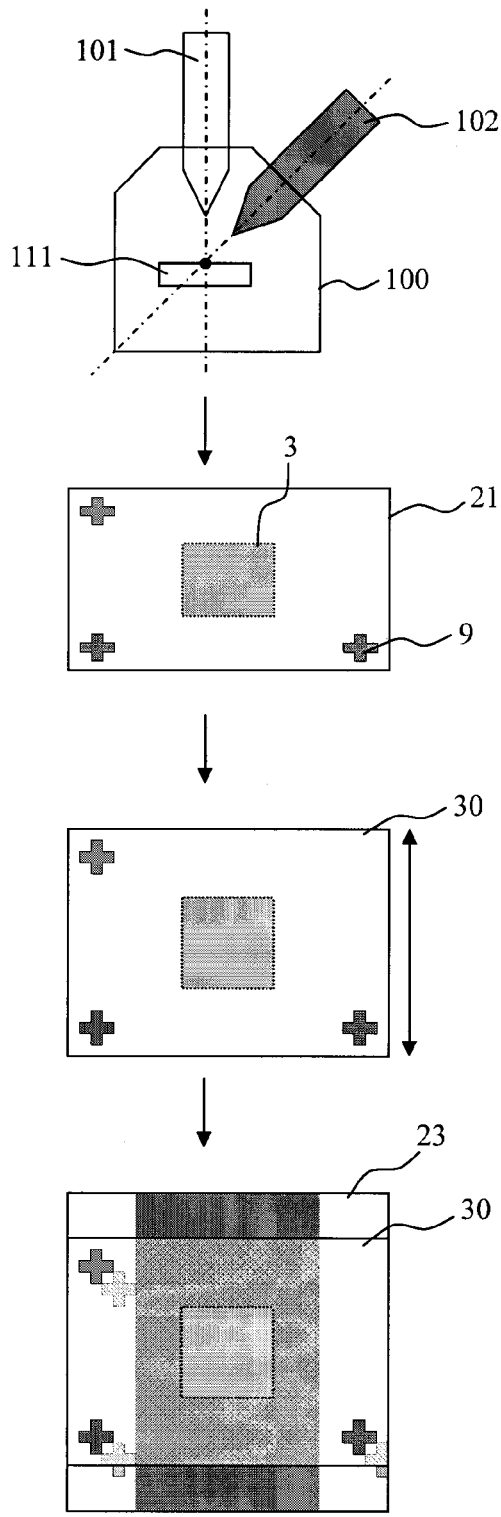
FIG. 24 is a drawing used to describe a method for making the tilt correction of an SEM image obtained from a direction of tilt with respect to a sample surface, and superimposing the SEM image on an FIB image.

On the other hand, FIG. 24 illustrates a case of not performing angular corrections by driving the sample stage 104 (sample 111). In this case, an SEM image 21 compressed in the vertical direction, for example, is acquired when an electron beam is scanned onto the sample 111 from a direction of tilt. Hence, image processing is applied to the SEM image 21 to generate an SEM image 30 the aspect ratio of which has been corrected so as to eliminate effects of inclination. Image processing is performed by, for example, a computing processor 110. Note that a corrective expression can be calculated using a tilt angle between the sample 111 and the beam axis.

After this, an FIB image 23 (including a non-ion beam scanned region 10 and ion beam-scanned regions 11) is acquired using the focused ion beam column 101 the beam axis of which is perpendicular to the sample 111. Then, the FIB image 23 and the SEM image 30 are aligned with each other, so that the singular points 9 of the FIB image 23 and the singular points 9 of the SEM image 30 overlap with each other. In this case, the amount of time taken to superimpose the two images can be shortened since the sample stage 104 need not be driven.

Note that FIG. 24 illustrates an example in which the focused ion beam column 101 is disposed so that the beam axis thereof is perpendicular to the sample 111, and the electron beam column 102 is disposed so that the beam axis thereof is tilted with respect to the sample 111. The relationship between each beam axis and the sample 111 is not limited this example, however. Alternatively, for example, the focused ion beam column 101 may be disposed so that the beam axis thereof is tilted with respect to the sample 111, and the electron beam column 102 may be disposed so that the beam axis thereof is perpendicular to the sample 111. Yet alternatively, the focused ion beam column 101 and the electron beam column 102 may be disposed so that both beam axes thereof are tilted with respect to the sample 111.

Also note that respective embodiments including this Embodiment 4 assume a charged particle beam device 100 having a double-column configuration comprising one focused ion beam column and one electron beam column. However, the processing technique of each embodiment can also be applied to a charged particle beam device having a triple-column configuration comprising a gallium (Ga) focused ion beam column, an argon (Ar) focused ion beam column, and an electron beam column.

Alternatively, switching control may be performed by switching among deflection patterns, rather than by selectively performing switching control on the tilt angle and the height of the sample stage 104 depending on whether the focused ion beam column 101 or the electron beam column 102 is used. In this case, the charged particle beam device 100 is provided with a function to convert the deflection pattern of the focused ion beam to a deflection pattern of the electron beam or convert the deflection pattern of the electron beam to a deflection pattern of the focused ion beam, on the basis of an angle formed by the beam axis of a focused ion beam and the beam axis of an electron beam, a perpendicular line of a plane formed by the beam axis of the focused ion beam and the beam axis of the electron beam, and an angle formed by the deflection scanning directions of respective beams.

(5) Embodiment 5

As Embodiment 5, a description will be given of another application example to which a charged particle beam device 100 is suitably applied. That is, a description will be given of a case of applying the charged particle beam device 100 to the fabrication of a protective film at the time of microsampling, rather than applying the charged particle beam device 100 to the processing of the sample 111, as in the above-described four embodiments.

Figure 25:
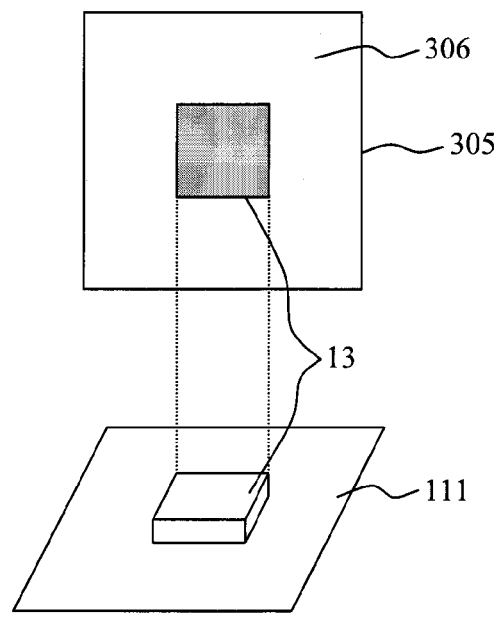
FIG. 25 is a drawing used to describe a case of applying a charged particle beam device to the fabrication of a protective film.
Figure 25:
Figure 25:
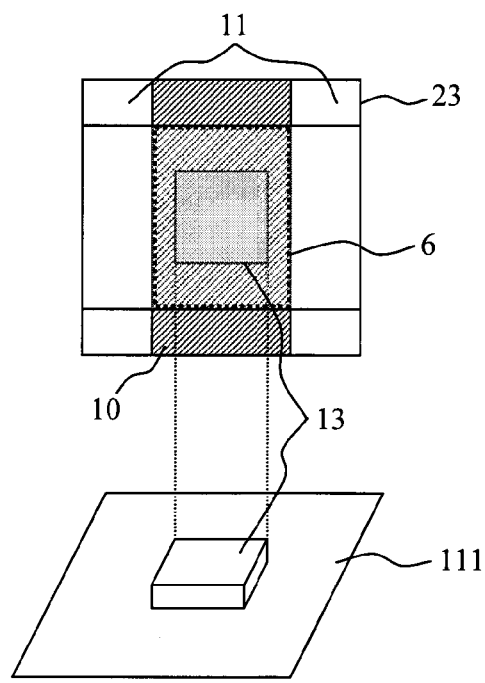

First, a conventional example is illustrated in the upper section of FIG. 25. In the case of the conventional example, the entire surface of a sample 111 needs to be set as an ion beam-scanned region 305, in order to specify the position to fabricate a protective film 13 in. In addition, a prearranged region for the protective film 13 to be fabricated in is scanned with a focused ion beam at least once to acquire an FIB image 306. After this, the position to fabricate the protective film 13 in is specified on the basis of the FIB image 306 to fabricate the protective film 13 on the sample 111 by ion beam irradiation. However, damage is caused to the region for the protective film 13 to be fabricated in, by ion beam irradiation at the time of acquiring the FIB image.

Next, the embodiment is illustrated in the lower section of FIG. 25. In the case of the embodiment, the ion beam-scanned region 11 is set, so as to avoid the prearranged region for the protective film 13 to be fabricated in, and the region is irradiated with an ion beam to acquire the FIB image 23. Then, part of a missing portion (non-ion beam scanned region 10) of the FIB image 23 is superimposed on a complementary image 6 (part of a captured image 20). Consequently, the observation of a corresponding region is enabled without having to irradiate an ion beam onto the prearranged region for the protective film 13 to be fabricated in. Consequently, the position to fabricate the protective film 13 in can be specified without causing any damage by an ion beam.

(6) Embodiment 6

In the above-described embodiment, a description has been given of a composite charged particle beam device 100. However, the charged particle beam device 100 is not limited to a composite type. For example, the aforementioned techniques can also be applied to a charged particle beam device including only a focused ion beam column 101. In this case, a design-time pattern image, an image already acquired in another process, or a charged particle beam image of a target region, for example, may be adopted as the complementary image 6 for the FIB image.

REFERENCE SIGNS LIST

1: Captured image, 2: Singular point, 3: Ion beam irradiation-prohibited region, 4: FIB image, 6: Complementary image, 7: Processed region, 9: Singular point, 10: Non-ion beam scanned region, 11: Ion beam-scanned region, 13: Protective film, 20: Captured image, 23: FIB image, 28: Non-ion beam irradiated region, 30: SEM image, 100: Charged particle beam device, 101: Focused ion beam column, 102: Electron beam column, 103: Vacuum sample chamber, 104: Sample stage, 105: Probe, 106: Probe driver, 108: Detector, 109: Display, 110: Computing processor, 111: Sample, 112: Nozzle tip, 115: Deposition gas source, 121: Ion beam control means, 122: Electron beam control means, 123: Detector control means, 124: Stage control means, 125: Deposition gas source control means, 126: Probe control means, 200: Display unit, 201: Input unit, 202: Control unit, 203: GUI controller, 204: FIB controller, 205: SEM controller, 206: Device main unit, 207: FIB image memory, 208: SEM image memory, 209: Image superimposition control, 210: Input control, 211: Image display control, 221: Control signal, 222: Luminance data, 223: Control signal, 224: Luminance data, 225: FIB image data, 226: SEM image data, 227: Input signal, 228: Information, 229: Superimposed image data, 230: Display signal, 305: Ion beam-scanned region, 306: FIB image.

The invention claimed is:
1. A charged particle beam device comprising:
a deflector for deflectively scanning a charged particle beam,
a display unit for detecting particles generated by irradiation of the charged particle beam and displaying an image, and
a controller for controlling a deflection pattern of the charged particle beam, wherein the controller includes:

a first memory for storing a first image obtained by scanning a scanning region set outside an ion beam irradiation-prohibited region with an ion beam;

a second memory for storing a second image obtained by scanning a capturing region set so as to overlap with at least part of the irradiation-prohibited region and at least part of the scanning region with a charged particle beam other than an ion beam; and means for complementarily superimposing the first and second image, wherein the display unit displays a superimposed image obtained by superimposing the first and the second image, and wherein a region of a sample to be processed with the ion beam is set within the superimposed image.

2. The charged particle beam device according to claim 1, further comprising means for controlling the attitude of a sample stage, on the basis of an angle formed by the observation directions of the first image and the second image, if the observation direction of the first image based on the ion beam and the observation direction of the second image based the charged particle beam differ from each other.

3. The charged particle beam device according to claim 1, wherein the deflection pattern of the ion beam is converted to the deflection pattern of the charged particle beam and vice versa, on the basis of an angle formed by the observation directions of the first image and the second image, a perpendicular line of a plane formed by the first observation direction and the second observation direction, and an angle formed by the deflection scanning directions of the ion beam or the charged particle beam other than the ion beam, if the observation direction of the first image based on the ion beam and the observation direction of the second image based the charged particle beam differ from each other.

4. The charged particle beam device according to claim 1, wherein the first and second images are superimposed so that an image of a first position correction mark acquired from the first image and a second position correction mark acquired from the second image align with each other.

5. The charged particle beam device according to claim 4, wherein the first and second images are superimposed on each other by moving one of the first and second images.

6. The charged particle beam device according to claim 4, wherein the first and second images are superimposed on each other by expansionally transforming one of the first and second images.

7. The charged particle beam device according to claim 4, wherein the first and second images are superimposed on each other by contractionally transforming one of the first and second images.

8. The charged particle beam device according to claim 4, wherein the first and second images are superimposed on each other by rotationally transforming one of the first and second images.

9. The charged particle beam device according to claim 1, wherein the processing position of a processing pattern for extracting a minuscule test piece from a sample mounted on the sample stage can be registered.

10. The charged particle beam device according to claim 1, wherein a fabrication position of a protective film pattern for extracting a minuscule test piece from a sample mounted on the sample stage can be registered.

11. A position specification method used in a charged particle beam device provided with a deflector for deflectively scanning a charged particle beam, a display unit for detecting particles generated by irradiation of the charged particle beam and displaying an image, and a controller for controlling a deflection pattern of the charged particle beam, the method comprising the steps of:

acquiring a first image obtained by scanning a scanning region set outside an ion beam irradiation-prohibited region with an ion beam;

acquiring a second image by scanning a capturing region set so as to overlap with at least part of the irradiation-prohibited region and at least part of the scanning region with a charged particle beam other than an ion beam;

complementarily superimposing the first and the second image;

displaying a superimposed image obtained by superimposing the first image and the second image; and setting a region of the sample to be processed with the ion beam within the superimposed image.

12. A program configured to allow a computer to execute position specification processing of a charged particle beam device provided with a deflector for deflectively scanning a charged particle beam, a display unit for detecting particles generated by irradiation of the charged particle beam and displaying an image, and a controller for controlling a deflection pattern of the charged particle beam, to perform the steps of:

acquiring a first image obtained by scanning a scanning region set outside an ion beam irradiation-prohibited region with an ion beam;

acquiring a second image by scanning a capturing region set so as to overlap with at least part of the irradiation-prohibited region and at least part of the scanning region with a charged particle beam other than an ion beam;

complementarily superimposing the first image and the second image;

displaying a superimposed image obtained by superimposing the first image and the second image; and setting a region of the sample to be processed with the ion beam within the superimposed image.

* * * * *